(12) United States Patent
Apel et al.

(10) Patent No.: US 7,074,730 B2
(45) Date of Patent: Jul. 11, 2006

(54) BIOACTIVE RHENANITE GLASS CERAMIC

(75) Inventors: Elke Apel, Buchs (CH); Wolfram Höland, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 150 days.

(21) Appl. No.: 10/777,516

(22) Filed: Feb. 12, 2004

(65) Prior Publication Data

US 2004/0167006 A1 Aug. 26, 2004

(30) Foreign Application Priority Data

Feb. 21, 2003 (DE) ................................ 103 07 646

(51) Int. Cl.
*C03C 10/02* (2006.01)
*A61K 6/033* (2006.01)
(52) U.S. Cl. .......................................... 501/10; 106/35
(58) Field of Classification Search ................. 501/10; 106/35
See application file for complete search history.

(56) References Cited

U.S. PATENT DOCUMENTS

2004/0175430 A1* 9/2004 Berger et al. ............... 424/602

2004/0228927 A1* 11/2004 Berger et al. ............... 424/602

FOREIGN PATENT DOCUMENTS

| DE | 23 26 100 C3 | 12/1974 |
| DE | 41 13 021 A1 | 10/1992 |
| DE | 691 28 621 T2 | 2/1998 |
| DE | 197 25 555 A1 | 12/1998 |
| WO | WO 01/12242 A1 | 2/2001 |

OTHER PUBLICATIONS

Hench, "A Genetic Theory of Bioactive Materials," *Key Engineering Materials*, 192-195:575-580 (2001).
Suchanek et al., "β-Rhenanite (β-NaCaPO$_4$) as Weak Interphase for Hydroxyapatite Ceramics," *J. European Ceram. Soc.*, 18:1923-1929 (1993).
Hench, "Bioceramics: From Concept to Clinic," *J. Am. Ceram. Soc.*, 74(7):1487-1510 (1991).

* cited by examiner

*Primary Examiner*—Karl Group
(74) *Attorney, Agent, or Firm*—Nixon Peabody LLP

(57) ABSTRACT

The invention relates to a bioactive rhenanite glass ceramic which is characterized by a high content of $P_2O_5$, CaO and $Na_2O$ and is particularly suitable as bone replacement material in dentistry.

26 Claims, No Drawings

BIOACTIVE RHENANITE GLASS CERAMIC

The invention relates to a bioactive rhenanite-containing glass ceramic which is characterized by a high content of $P_2O_5$, CaO and $Na_2O$ and is particularly suitable as bone restorative material in dentistry or as restorative material for dentine or tooth enamel.

Bioactive glasses and glass ceramics are known from the state of the art. On the one hand these are materials which are based on a siliceous base system and have $P_2O_5$ as additional component and on the other hand the group of the $SiO_2$-free phosphate glasses and glass ceramics. Characteristic for these materials is the presence of a glassy-amorphous base matrix and, in the case of the glass ceramics, additionally one or more crystalline phases.

Moreover there is the group of crystalline, glass-free phosphates which, as single or multi-component systems, are used as bone restorative material and have an excellent resorbability.

Only one surface reactivity mechanism forms the basis of all these known material groups, as the following explanations show.

The bioactive, $SiO_2$-containing glass ceramics for bone restoration have mainly apatite crystals as essential phase for promoting the regeneration of living bone. They are used for bone restoration in human medicine and dentistry in such a way that they provide a reactive surface layer, which for its part promotes the additional formation of apatite crystals. This group of apatite-containing siliceous glass ceramics includes e.g.

Cerabone®: apatite-wollastonite-glass ceramic
Ceravital®: apatite-glass ceramic
Bioverit II®: apatite-mica-glass ceramic Bioactive glasses, i.e. materials without crystals, are likewise known. Bioglass® and Perioglass® are representatives of the substance system $Na_2O$—CaO—$SiO_2$—$P_2O_5$. Hench (*J. Am. Ceram. Soc.*, 74 (1991) 1487–1510) describes the direct intergrowth between such glasses with the natural bone in 11 reaction steps. A quick surface reaction which is connected to the release of Ca–, Na–, P– and other ions is typical for these materials. This high solubility has a disadvantageous effect however on the mechanical strength of the bioactive glasses. The use as bone restoration with load-bearing functions, e.g. for the replacement of dorsal vertebrae, is thus not possible in contrast to the apatite-wollastonite glass ceramics.

A further disadvantage of bioactive glasses is that the granular particles, due to their high solubility in body fluids, are transported away from the implantation site and from its surroundings before new bone can form.

Peitl et al. (*J. Noncryst. Solids*, 292 (2001) 115–126) describes a glass ceramic based on Bioglass® which contains a phosphate-free crystalline phase ($NaCa_2Si_3O_9$) and a phosphate-containing residual glass matrix. It has an improved bioactivity vis-à-vis the named bioglass ceramics and, in a solution based on human body fluid, Simulated Body Fluid (SBF), leads to the formation of hydroxyl carbonate apatite (HCA).

A completely resorbable $SiO_2$-free glass ceramic is furthermore known from DE-A-41 13 021 with Bioverit® III. It contains apatite and $AlPO_4$ as main crystal phases as well as other complex phosphates. It has however the serious disadvantage that it contains $Al^{3+}$ ions which are disruptive for the biological system of bone regeneration. The result of this is that as of a certain concentration, the formation of apatite is made more difficult or is even completely prevented.

In WO 01/12242 completely glass-free, crystalline phosphate compounds, such as e.g. $Ca_2NaK(PO_4)_2$ and $CaKPO_4$, are likewise described as biomaterials. These sodium potassium or potassium-calcium phosphates improve biological degradability and bone regeneration. $Ca_2KNa(PO_4)_2$ is very well suited to healing bone defects, as was described by Niu Jinlong et al. (*J. Mat. Science* 36 (2001) 3805–3808) and G. Berger et al. (*Biomaterials* 16 (1995) 1241–1258). However these crystalline materials have the disadvantage that they have a very high decomposition and conversion rate. As a result the storage stability of these materials and also the processing time during clinical application is extremely short. The possibilities of moulding are also limited vis-à-vis glasses and glass ceramics.

Rhenanite or rhenanite in combination with other known crystal phases, particularly hydroxyl apatite, has likewise already been described as bone restorative material.

The bioactive properties of pure β-$NaCaPO_4$, i.e. rhenanite, were described in works by Driessens et al. (*J. Mat. Science*, 3 (1992) 413–417) and Suchanek et al. (*J. Europ. Cer. Soc.* 18 (1998) 1923–1929). According to these, rhenanite displays osteoconductivity in SBF, i.e. a high level of efficiency and quality as bone restorative material.

Rhenanite appears in calcium phosphate glasses and glass ceramics along with apatite and further crystalline calcium phosphate phases as a secondary phase. Zhang et. al. (*J. Non-Cryst. Solids* 272 (2000) 14–21) describe the formation of rhenanite in a phosphate-containing, $SiO_2$-free base system with addition of at most 5 mol % $Na_2O$.

Rhenanite is furthermore described in DE-A-197 25 555 as possible secondary crystal phase in a translucent apatite-leucite glass ceramic which is used as facing material for ceramic dental restorations. This glass ceramic is however not surface-reactive, i.e. not bioactive, and it contains $Al_2O_3$ which is disadvantageous for the biological system.

The object of the invention is therefore to make available a bioactive glass ceramic which, in contrast to other $SiO_2$-containing systems, is characterized in particular by an adjustable chemical kinetics for the formation of apatite in SBF on the surface of the material. Furthermore the glass ceramic should also be able to be produced even without contents of biologically disadvantageous substances such as Al compounds.

This object is surprisingly achieved by the bioactive rhenanite glass ceramic according to claims 1 to 12.

The process according to claim 13, the shaped bodies according to claims 14 and 15, the use according to claim 16 and the bioactive composite material according to claim 17 also constitute subject-matter of the invention.

The bioactive rhenanite glass ceramic according to the invention with crystalline phase and glass phase is characterized in that the crystalline phase contains rhenanite and the glass ceramic contains the following components:

| Components | Amount (wt. - %) |
|---|---|
| $SiO_2$ | 29.5 to 70.0 |
| CaO | 5.5 to 23.0 |
| $Na_2O$ | 6.0 to 27.5 |
| $P_2O_5$ | 2.0 to 23.5 |
| F | 0 to 1.5 | and is essentially free of $Al_2O_3$.

In the glass ceramics according to the invention, rhenanite, i.e. β-$NaCaPO_4$, preferably forms, the main crystal phase. The bioactive residual glass phase contributes to a quick apatite formation due to its high solubility in SBF, while the osteoconductive-acting rhenanite crystal phase leads to a slower apatite formation, but guarantees an improved mechanical stability of an implant. This double mechanism of the reactivity of the glass ceramic makes possible the control of the bioactivity and is a particular advantage of the glass ceramic according to the invention.

The glass ceramic according to the invention preferably contains less than 0.1 wt.-% $Al_2O_3$, particularly preferably less than 0.01 wt.-% $Al_2O_3$ and is quite particularly preferably free from $Al_2O_3$. $Al_2O_3$ could, as described above, reduce the bioactivity of the glass ceramic and the formation of apatite.

The solubility of the glass ceramic is lower compared with the known bioglasses described above. This reduced solubility prevents it from being transported away from the implantation site, before new bone can form. In addition the decomposition and conversion rates are also not as high as with the glass-free phosphates in which the processing time and the storage stability of biocompatible materials are limited by the rapid chemical kinetic materials conversion for apatite formation.

As a result of the variation of the crystalline proportion of rhenanite in the glass ceramic, a control of the chemical kinetics of the apatite formation is possible, and glass ceramics which contain between 4 and 50 wt.-%, in particular between 10 and 50 wt.-% or between 4 and 40 wt.-% rhenanite are preferred.

Preferred is a glass ceramic according to the invention which contains the following components independently of one another in the following amounts:

| Components | Amount (wt. - %) |
| --- | --- |
| $SiO_2$ | 29.5 to 65.5 |
| CaO | 6.0 to 23.0 |
|  | (in particular 11.0 to 23.0) |
| $Na_2O$ | 7.0 to 25.5 |
| $P_2O_5$ | 3.0 to 23.5 |
|  | (in particular 5.5 to 23.5) |
| F | 0.5 to 1.2. |

The term "independently of one another" means that only at least one of the preferred quantity ranges can also be selected.

Quite particularly preferred is a glass ceramic which contains the following components independently of one another in the following amounts:

| Components | Amount (wt. - %) |
| --- | --- |
| $SiO_2$ | 35.0 to 60.0 |
| CaO | 15.0 to 23.0 |
| $Na_2O$ | 9.0 to 25.5 |
|  | (in particular 7.0 to 18.0) |
| $P_2O_5$ | 10.0 to 23.5 |
|  | (in particular 10.0 to 20.0) |
| F | 0.5 to 1.2. |

Such a rhenanite glass ceramic is characterized in particular by a high surface reaction for the formation of phosphates, in particular apatite, in SBF.

It is advantageous if the glass ceramic contains at least one of the following additional components, which are different from the afore-mentioned components, in order to influence the following properties in a controlled manner.

For an improvement of the biological reactivity additions of the oxides of K, B, Ti, Zr, Nb, Ta have proved useful. In this case the oxides of the elements Ti, Zr, Nb and Ta form reactive OH-groups. The oxides of B generally show a high bio-compatibility. K is introduced instead of Na into the rhenanite and reinforces the crystalline phases via the formation of mixed crystals.

For enhancing of the x-ray opacity, additions of the oxides of the elements Nb, Ta, Y and La have proved successful.

An antimicrobial activity is achieved by the addition of Ag, Zn and Y to the glass ceramic.

| Components | Amount (wt. - %) |
| --- | --- |
| $R^{(I)}_2O$ | 0 to 15.0 |
| $R^{(II)}O$ | 0 to 4.0 |
| $R^{(III)}_2O_3$ | 0 to 10.0 |
| $R^{(IV)}O_2$ | 0 to 10.0 in particular up to 1.0 |
| Hal | 0 to 2.0 | wherein
$R^{(I)}$represents a monovalent cation, in particular K or Ag
$R^{(II)}$represents a divalent cation, in particular Zn
$R^{(III)}$represents a trivalent cation, in particular B, Nb, Ta, Y, La or a lanthanoid,
$R^{(IV)}$represents a quadrivalent cation, in particular Ti, and Hal represents a halogenid ion, in particular Br or I.

If additional components are present, their amount in the glass ceramic is at least 0.1 wt.-%.

Particularly preferred are glass ceramics which consist of the previously stated components and optionally the mentioned additional components.

It is furthermore advantageous in the glass ceramic according to the invention if the weight ratio of $Na_2O$:CaO is from 0.8 to 2.0 and the weight ratio of CaO:$P_2O_5$ is from 0.9 to 2.2. This is in particular advantageous if spontaneously crystallizing glass ceramics are to be produced.

It is also advantageous in the glass ceramic according to the invention if the weight ratio of $Na_2O$:CaO is from 1.0 to 2.1 and the weight ratio of CaO:$P_2O_5$ is from 0.9 to 2.2. This is in particular advantageous, if glass ceramics are to be produced the production of which requires a heat treatment.

It is in addition advantageous if the crystalline phase of the glass ceramic according to the invention additionally contains at least one of the following crystalline components: sodium calcium silicate, apatite, sodium phosphate, sodium calcium phosphate and sodium potassium calcium phosphate.

Preferred is a rhenanite glass ceramic in which the rhenanite crystals are at most 10 μm in size. Furthermore a rhenanite glass ceramic is preferred in which the rhenanite crystals have an average size (numerical average) between 0.01 and 5.0 μm. Quite particularly preferably the average size is between 0.15 and 2.5 μm, as the bioactivity is positively influenced by resorption processes. In this preferred sizes the reaction kinetics of the dissolution and the conversion of the rhenanite crystals is particularly facilitating the growing-in of an implant. It was possible to obtain through crystallization crystals in the nanoscale of an average size (nummerical average) of 0.01 to 5.0 μm. It was possible by process control to obtain isolated crystals in the remaining glass matrix or agglomerates by growing of new crystals as seperate crystals on the surface of already formed crystals and not by increasing the size of already formed crystals.

For the production of the glass ceramic according to the invention
- a) a starting glass with a composition, which contains the components and optionally additional components, is melted at temperatures of 1200° C. to 1650° C.,
- b) the glass melt from a) is cooled, in particular the glass melt is
  - (i) poured into water, a glass granulate thus forming or
  - (ii) poured into a mould or
  - (iii) quenched between metal plates,
- c) optionally the cooled glass from b) is heat treated at temperatures of 600° C. to 1000° C., in particular 600° C. to 980° C., for a period from 10 minutes to up to 10 hours, in particular up to 8 hours, and
- d) optionally the glass ceramic, which results from b) or c), is ground to a powder with a particle size of 100 nm to 100 µm, preferably 1 to 50 µm.

With higher phosphate contents, above 6 wt.-% $P_2O_5$, the starting glass is expediently first heated from room temperature to 1200° C. in roughly one hour in an Al-free crucible and then cooled. This thus-produced sinter cake is then melted instead of the starting glass, as described above, in the Pt-Rh-crucible at 1200 to 1650° C.

In the production of the glass ceramic according to the invention, the rhenanite can be produced both by subsequent crystallization using heat treatment of the starting glass in step (c) and by spontaneous crystallization when cooling the glass from the melt in step (b). The crystallization of the rhenanite is determined decisively by the ratio $Na_2O$:CaO and the phosphate content in the composition.

During the spontaneous crystallization the rhenanite can occur as only crystal phase or also, depending on the compositions, together with silicates (inter alia $Na_2SiO_5$, $Na_2CaSi_3O_8$, $NaCa_2Si_3O_9$, $NaCa_3Si_6O_{16}$) or other phosphates like ($Na_3PO_4$, $Na_2Ca(PO_4)F$, $KNaCa_2(PO_4)_2$, $KCa(PO_4)_4$, $Ca_5(PO_4)_3F$).

From starting glasses with a high tendency towards phase separation, rhenanite crystallizes from the segregation drops during heat treatment. The crystals are preferably between 0.01 and 0.5 µm in size in numerical average. The crystal phase has in particular a proportion of 4 to 50 wt.-%. Longer tempering times or higher temperatures lead to coarser structures. The initially individual drops join together in pairs and join together in chains. The preferred heat treatment in step (c) takes place for compositions with low phosphate contents in the temperature range of 650 to 750° C. with holding times of 1 to 6 hours and for compositions with nanocrystal separations in the temperature range of 650 to 1000° C. in a one- or multi-step process of thermal treatment for 0.5 to 10 hours.

In the case of spontaneous crystallization larger swarms with branched structures form. A composite structure or penetrative structure preferably forms wherein coarser crystals with a thickness of 0.2 to 0.8 µm and a length of 1.0 to 5.0 µm are present.

Depending on the composition and cooling conditions, extremely fine crystals (0.05 µm diameter) are produced from the melt which therefore have a nano-crystalline structure.

The amount of crystalls for all types of glass ceramics according to the invention is preferably about 4 to 50% by weight.

Shaped bodies which contain the glass ceramic according to the invention and in particular are composed of it are a further part of the present invention. These shaped bodies are preferably monolithic, i.e. dense or porous bodies with open pores with a pore diameter of roughly 2 to 200 µm. These are in particular bone implants, in particular for the dental field.

The invention relates in addition to a process for the production of a shaped body made of the glass ceramic according to the invention, in which the glass ceramic according to the invention is firstly shaped as desired and the obtained shaped body sintered after pressing for a period of roughly 30 minutes at 600° C. to 750° C.

To produce shaped bodies it is likewise possible to grind a starting glass with a composition which contains the above-named components of rhenanite glass ceramic and optionally the above-named additional components, to the desired particle size with the desired particle size distribution, a numerical average of the particle size of 1 to 50 µm being preferred and the particle size distribution being able to be mono-, bi- or trimodal, and to produce blanks from the powders which are then sintered to dense shaped bodies in a predetermined time and temperature interval, e.g. 30 minutes at 600° C. As a result of this heat treatment the crystallization of the glass and thus the formation of the glass ceramic can be effected.

A shaped body with open pores can be produced according to the process described by Kim et al. in Biomaterials 24, 3277–3284 (2003) by coating the internal surface of the pores of a plastic foam, for example a polyurethane foam, with a highly-liquid dispersion with a particle size of the glass ceramic particles of smaller then 300 µm. Subsequently, the plastic foam is fired with a small heating rate up to 700° C. The result is a ceramic framework ("scaffold") having open pores of a diameter of about 100 to 200 µm.

The use of the glass ceramic according to the invention as material for the reconstruction of bone and/or for restoration of bones, in particular in dentistry, i.e. as dental material or as restorative material for natural tooth material, in particular dentine or tooth enamel, is likewise a part of the invention.

The glass ceramic according to the invention is preferably used to promote bone growth, in particular in dentistry. It can be used in a advantageous manner for example in the area surrounding metal implants, as bioactive layer of biocompatible materials, as pulp protector, as dentine and tooth enamel restorative material in form of an addition to a dental care product like a toothpaste, as framework and/or supporting material for bioactive ingredients, such as growth factors, hormones, proteins, polypeptides and saccharides and others or as active ingredient having bacteriostatic or therapeutic activity with controlled release of ions and/or release of active ingredient.

The glass ceramic according to the invention can also be used in combination with organic compounds. In this case it is used in particular in monolithic form, powder form or porous form. The organic compounds can be biopolymers, which are based on hydroxy acids or cyclic carbonates, lactates and/or acryl amides. Such combinations are useful as bioactive composite materials in particular in dentistry. The invention therefore relates also to such bioactive composite materials.

The invention is explained further in the following using examples:

EXAMPLES 15 different glasses of the $SiO_2$—$Na_2O$—CaO—$P_2O_5$ system were produced and, depending on the composition, either by cooling of the composition in a controlled manner crystallized or directly crystallized during the cooling process. The compositions of the glasses are given in Table 1. All samples were melted at temperatures of 1200° C. to 1650° C. as 120 g batches in the Pt/Rh crucible. Depending on the composition the melting time was 1 to 3 hours. Rods with an 11 mm diameter and 55 mm length were poured from the melt into preheated steel moulds.

TABLE 1

| No. | SiO$_2$ | CaO | Na$_2$O | P$_2$O$_5$ | F | K$_2$O |
|---|---|---|---|---|---|---|
| 1 | 62.4 | 12.9 | 14.6 | 10.1 | 0 | 0 |
| 2 | 70.0 | 8.0 | 16.0 | 5.5 | 0.5 | 0 |
| 3 | 69.3 | 16.2 | 6.2 | 7.5 | 0.8 | 0 |
| 4 | 60.4 | 5.5 | 26.9 | 6.5 | 0.7 | 0 |
| 5 | 29.8 | 21.1 | 25.4 | 23.1 | 0.6 | 0 |
| 6 | 55.0 | 12.5 | 25.0 | 6.3 | 1.2 | 0 |
| 7 | 39.8 | 22.7 | 27.3 | 9.6 | 0.6 | 0 |
| 8 | 55.8 | 12.4 | 25.0 | 6.3 | 0.5 | 0 |
| 9 | 59.3 | 13.7 | 20.1 | 6.3 | 0.6 | 0 |
| 10 | 45.2 | 22.1 | 22.1 | 10.0 | 0.6 | 0 |
| 11 | 65.3 | 15.0 | 12.0 | 7.0 | 0.7 | 0 |
| 12 | 54.7 | 16.3 | 19.4 | 9.0 | 0.6 | 0 |
| 13 | 35.1 | 22.0 | 22.0 | 20.0 | 0.9 | 0 |
| 14 | 35.1 | 22.0 | 9.4 | 20.0 | 0.9 | 12.6 |
| 15 | 58.9 | 12.5 | 25.0 | 3.0 | 0.6 | 0 |

In the case of the glasses according to Examples 1, 2, 4 and 6 to 10 as well as 15 the rhenanite crystallizes by subsequent heat treatment at 750° C. for 2 to 8 hours and rhenanite glass ceramics according to the invention form. In the case of the glasses according to Examples 3, 5 and 11 to 14 the rhenanite, after being poured into a mould, crystallizes spontaneously from the melt upon cooling accompanied by the formation of rhenanite glass ceramics according to the invention.

In Table 2 the conditions are given for Examples 8, 10, 13, 14 and 15 (melting temperature and period) under which the respective starting glasses were melted. The table also gives the appearance of the materials after cooling. For the non-spontaneously crystallizing glasses of Examples 8 and 10 details of the heat treatment are also given. Finally, the respective glass ceramics are described with regard to their material properties and in particular their crystal phases and rhenanite proportions as well as their ability to effect the formation of apatite in SBF.

In particular for example 8 a microstructure with homogeneously distributed crystallites in the nano-region with an average crystal size of about 200 nm was achieved. It was obtained by a thermal treatment at 900° C./1 h. In case of example 15 a rhenanite glass ceramic having nano-crystals with a size of about 20 to 100 nm was obtained by a controlled crystallization at 750° C./8 h and 900° C./1 h.

Using differential thermal analysis (Netzsch STA 409 PC) the transformation temperatures T$_g$ and the crystallization temperatures were determined. Glass or glass ceramic granules with a particle size of less than 90 μm were used for measurement. For the determination of the resulting crystallization in case of example 15 SEM photographs were taken as the DSC peaks were to small for the small crystal content of the glass ceramic or the measurements would otherwise have been to unprecise.

For the in vitro tests for apatite formation two solid plates of 11 mm diameter and 2 mm thickness were each prepared and stored in 50 ml SBF in sealed polyethylene bottles at 37° C. The SBF solution, also known as Kokubo solution Nr. 9, (see Kokubo et al. in *J. Biomed. Mater. Res.* 24 (1990) 721), was freshly prepared and adjusted to a pH-value of 7.3 at 37° C. with 45 mM HCl and 50 mM (CH$_2$OH)$_3$CNH$_2$.

After 24 hours the test pieces were examined for the formation of apatite by means of scanning electron microscopy (SEM) and energy-dispersive X-ray spectroscopy (EDX). Within 48 hours apatite formed in all test pieces. This shows the good bioactivity of the glass ceramics according to the invention and their particular suitability for use as dental material or for promoting bone growth.

Cell culture tests with SAOS-2 cells (human tumor cells) showed that even after one hour reaction time the cell starts to adhere to the surface of the glass ceramic according to the invention. After 24 hours the originally spherical cell is entirely flat and strongly adheres to the surface. Characteristic features for quick and advantageous bioactive processes of bone regeneration are the cell growth (proliferation) and cell differentiation observed during the cell culture tests. It has surprisingly been found that this process proceeds with the rhenanite glass ceramic according to the invention in an exponential fashion, a very advantageous property for biomaterials. A dying of cells was not observed. Moreover, the formation of hydroxyl apatite was observed in the cell culture tests and in tests in simulated body fluid (SBF). The later was observed in the same manner for monolithic and porous materials. The formed apatites were of needle form and aggregate to spherical aggregates. After 7 days a layer of hydroxyl apatite with a thickness of 0.5 μm was formed on the surface of the bioactive material. Apart from apatite, also octacalcium phosphate, a precursor of apatite, was observed as secondary crystalline phase.

TABLE 2

| | Number | | | | |
|---|---|---|---|---|---|
| | 8 | 10 | 13 | 14 | 15 |
| Melting temperature | 1400° C. | 1450° C. | 1550° C. | 1600° C. | 1400° C. |
| Melting period | 1.5 h | 1.0 h | 1.5 h | 1.0 h | 1.5 h |
| Appearance | Glassy Colourless Transparent | Glassy slightly segregated | white crystalline | white crystalline | Glassy Colourless Transparent |
| Heat treatment | 2 h/750° C. | 8 h/750° C. | none | none | 750° /8 h and 900° C./1 h |
| T$_g$ [° C.] | 500 | 540 | none | none | 500 |
| T crystallization [° C.] | 660 | 640/750 | 670 | 580/610 | ** |
| Crystal phase | β-NaCaPO$_4$ | β-NaCaPO$_4$ Na$_2$CaSi$_3$O$_8$ | β-NaCaPO$_4$ | β-NaCaPO$_4$ KNaCa$_2$(PO$_4$)$_2$ | β-NaCaPO$_4$ |
| Amount of rhenanite [wt. - %] | 13 | 22 | 45 | 47* | about 5 |
| Formation of apatite in SBF after | 24 h | 24 h | 48 h | 24 h | 24 h |

*for the glass ceramic No. 14 the proportion of β-NaCa (PO$_4$) and KNaCa$_2$ (PO$_4$)$_2$ together was 47 wt. - %
**identification of crystallization via SEM, crystal size of 20 to 100 nm

What is claimed is:

1. Bioactive rhenanite glass ceramic having a crystalline phase and a glass phase, the crystalline phase contains rhenanite and the glass ceramic contains the following components

| Components | Amount (wt. - %) |
| --- | --- |
| $SiO_2$ | 29.5 to 70.0 |
| CaO | 5.5 to 23.0 |
| $Na_2O$ | 6.0 to 27.5 |
| $P_2O_5$ | 2.0 to 23.5 |
| F | 0 to 1.5 | and is essentially free from $Al_2O_3$.

2. Glass ceramic according to claim 1, wherein the rhenanite is present in an amount between 4 and 50 wt.-%.

3. Glass ceramic according to claim 1, wherein the rhenanite is present in an amount between 10 and 50 wt.-%.

4. Glass ceramic according to claim 1, which contains the following component:

| Component | Amount (wt. - %) |
| --- | --- |
| $SiO_2$ | 29.5 to 65.5. |

5. Glass ceramic according to claim 1, which contains the following component:

| Component | Amount (wt. - %) |
| --- | --- |
| $SiO_2$ | 35.0 to 60.0. |

6. Glass ceramic according to claim 1, in which the weight ratio of $Na_2O$:CaO is from 1.0 to 2.1 and the weight ratio of CaO:$P_2O_5$ is from 0.9 to 2.2.

7. Glass ceramic according to claim 1, in which the weight ratio of $Na_2O$:CaO is from 0.8 to 2.0 and the weight ratio of CaO:$P_2O_5$ is from 0.9 to 2.2.

8. Glass ceramic according to claim 1, which further contains at least one of the following components:

| Components | Amount (wt. - %) |
| --- | --- |
| $R^{(I)}_2O$ | 0 to 15.0 |
| $R^{(II)}O$ | 0 to 4.0 |
| $R^{(III)}_2O_3$ | 0 to 10.0 |
| $R^{(IV)}O_2$ | 0 to 10.0 |
| Hal | 0 to 2.0 | wherein
$R^{(I)}$ represents a monovalent cation, in particular K or Ag
$R^{(II)}$ represents a divalent cation, in particular Zn
$R^{(III)}$ represents a trivalent cation, in particular B, Nb, Ta, Y, La or a lanthanoid,
$R^{(IV)}$ represents a quadrivalent cation, in particular Ti, and Hal represents a halogenid ion, in particular Br or I.

9. Glass ceramic according to claim 1, in which the crystalline phase further contains at least one of the following crystalline components: sodium calcium silicate, apatite, sodium phosphate, sodium calcium phosphate and sodium potassium calcium phosphate.

10. Glass ceramic according to claim 1, in which rhenanite crystals are at most 10 μm in size.

11. Glass ceramic according to claim 1, in which the rhenanite crystals have an average size (numerical average) of from 0.01 to 5.0 μm.

12. Glass ceramic according to claim 11, in which the rhenanite crystals have an average size (numerical average) of from 0.15 to 2.5 μm.

13. Shaped body which contains a glass ceramic according to claim 1.

14. Shaped body which consists of a glass ceramic according to claim 1.

15. Bioactive composite material which comprises the glass ceramic according to claim 1 and an organic compound.

16. Glass ceramic according to claim 4, wherein the CaO is present in an amount of from 11.0 to 23.0 wt.-%.

17. Glass ceramic according to claim 4, wherein the $P_2O_5$ is present in an amount of from 5.5 to 23.5 wt.-%.

18. Glass ceramic according to claim 5, wherein the $Na_2O$ is present in an amount of from 7.0 to 18.0 wt.-%.

19. Glass ceramic according to claim 5, wherein the $P_2O_5$ is present in an amount of from 10.0 to 20.0 wt.-%.

20. Glass ceramic according to claim 8, wherein the $R^{(IV)}O_2$ is present in an amount up to 1.0 wt.-%.

21. Glass ceramic according to claim 8, wherein the monovalent cation is K or Ag.

22. Glass ceramic according to claim 8, wherein the divalent cation is Zn.

23. Glass ceramic according to claim 8, wherein the trivalent cation is B, Nb, Ta, Y, La or a lanthanoid.

24. Glass ceramic according to claim 8, wherein the quadrivalent cation is Ti.

25. Glass ceramic according to claim 8, wherein the halogenid ion is Br or I.

26. Glass ceramic according to claim 12, wherein the rhenanite crystals have an average size (numerical average) of from 0.5 to 2.5 μm.

* * * * *